(12) United States Patent
Bruestle et al.

(10) Patent No.: US 9,017,262 B2
(45) Date of Patent: Apr. 28, 2015

(54) SYSTEMS AND METHODS FOR CONNECTION TO A TRANSDUCER IN ULTRASOUND PROBES

(75) Inventors: Reinhold Bruestle, Zipf (AT);
Wolfgang Dieter Knoll, Zipf (AT);
Christian Heinrich, Zipf (AT);
Christian Holl, Zipf (AT)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/342,168

(22) Filed: Jan. 2, 2012

(65) Prior Publication Data

US 2013/0172756 A1     Jul. 4, 2013

(51) Int. Cl.
*A61B 8/14*       (2006.01)
*A61B 8/00*       (2006.01)
*G01S 15/89*     (2006.01)

(52) U.S. Cl.
CPC ............ *A61B 8/4444* (2013.01); *A61B 8/4461* (2013.01); *G01S 15/8918* (2013.01); *G01S 15/8915* (2013.01); *G01S 15/892* (2013.01); *G01S 15/894* (2013.01); *G01S 15/8979* (2013.01)

(58) Field of Classification Search
CPC combination set(s) only.
See application file for complete search history.

(56) References Cited

U.S. PATENT DOCUMENTS

| | | | | |
|---|---|---|---|---|
| 1,477,966 | A * | 12/1923 | Lindstrom | 402/17 |
| 6,120,452 | A * | 9/2000 | Barthe et al. | 600/459 |
| 6,582,371 | B2 * | 6/2003 | Miller | 600/459 |
| 6,894,425 | B1 * | 5/2005 | Solomon et al. | 310/334 |

* cited by examiner

*Primary Examiner* — Long V Le
*Assistant Examiner* — Farshad Negarestan
(74) *Attorney, Agent, or Firm* — Dean Small; The Small Patent Law Group, LLC

(57) ABSTRACT

Methods and systems for connection to a transducer in ultrasound probes are provided. One connection arrangement includes a connector having a transducer connection portion configured to couple to a transducer of an ultrasound probe and a scan head connection portion configured to extend from a scan head of the ultrasound probe containing the transducer. The transducer connection portion and the scan head connection portion being a single element.

17 Claims, 8 Drawing Sheets

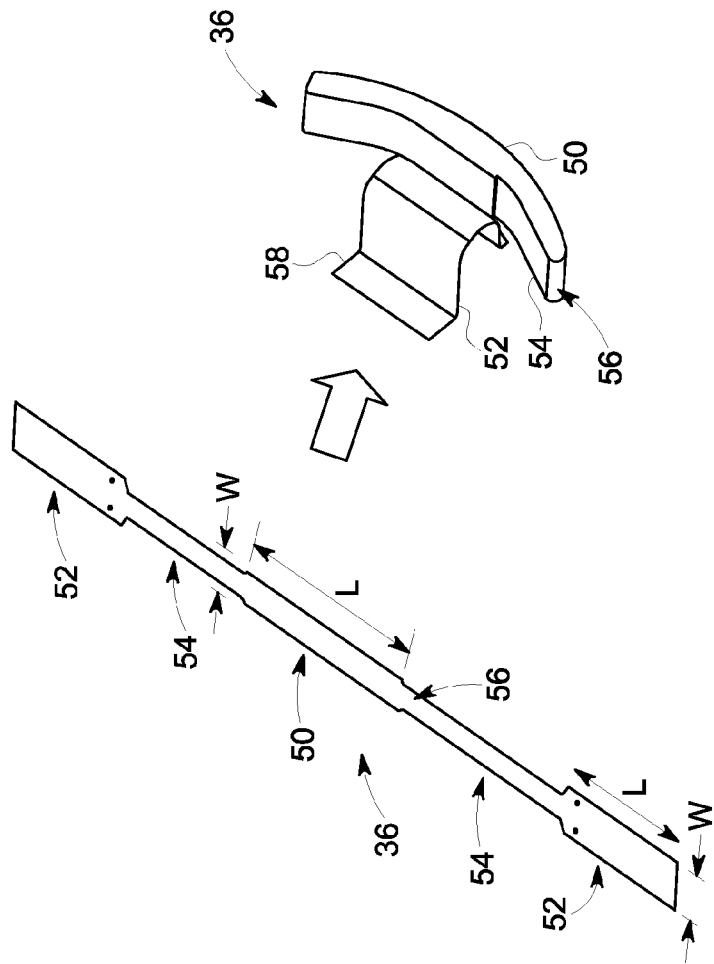
FIG. 5
FIG. 4
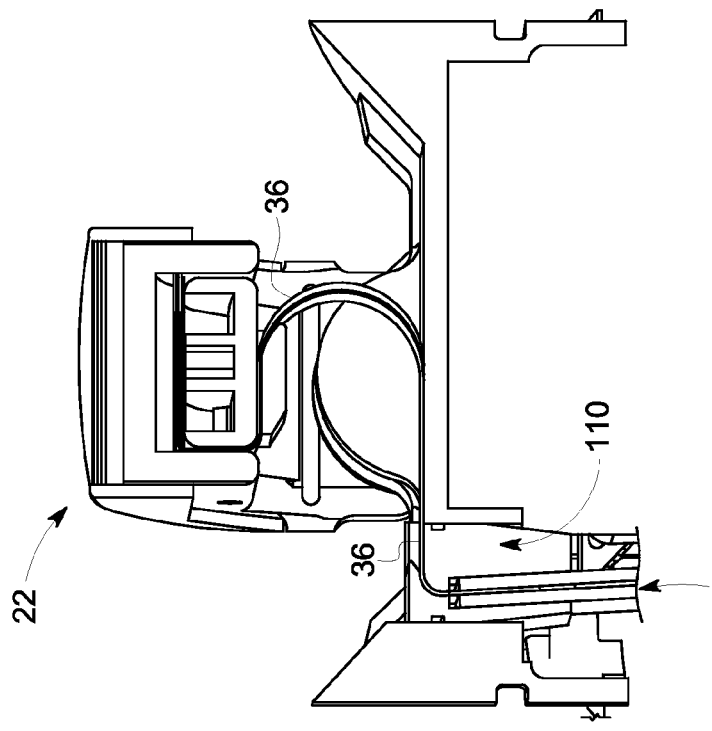
FIG. 3

SYSTEMS AND METHODS FOR CONNECTION TO A TRANSDUCER IN ULTRASOUND PROBES

BACKGROUND OF THE INVENTION

The subject matter disclosed herein relates generally to ultrasound systems and, more particularly, to probes for ultrasound medical imaging systems.

Ultrasound systems typically include ultrasound scanning devices, such as ultrasound probes having different transducers that allow for performing various different ultrasound scans (e.g., different imaging of a volume or body). The ultrasound probes are typically connected to an ultrasound system that controls the operation of the probes. The probes include a scan head having a plurality of transducer elements (e.g., piezoelectric crystals), which may be arranged in an array. The ultrasound system drives the transducer elements within the array during operation, such as, during a scan of a volume or body, which may be controlled based upon the type of scan to be performed.

In mechanical volume probes, often referred to as mechanical four-dimensional (4D) probes, the scan head mechanically moves during scanning operation. In these mechanical 4D probes, the mechanically moving transducer is interconnected to the non-moving portion of the probe to provide communication of signals to and from the transducer. The interconnections have to withstand considerable mechanical stress in the dynamic bending of the cable/flex interconnect.

In some conventional arrangements, separate interconnections are used to connect to the individual transducer elements. These interconnections have to meet certain acoustic requirements to avoid acoustic artifacts in imaging. These conventional interconnection arrangements use separate parts for the connection to the transducer elements and to the scan head. For example, some interconnection arrangements use coaxial cable assemblies for the scan head cable and connect to a separated flexible interconnection for connection to the transducer elements. This connection arrangement results in a larger probe and higher cost of manufacture.

Thus, the transducer connection and scan head connection in conventional arrangements requires additional interconnects and thus additional space within the probe. Accordingly, miniaturization of the probe is limited and the cost for the assembly is increased.

BRIEF DESCRIPTION OF THE INVENTION

In one embodiment, a connector for an ultrasound probe is provided. The connector includes a transducer connection portion configured to couple to a transducer of an ultrasound probe and a scan head connection portion configured to extend from a scan head of the ultrasound probe containing the transducer. The transducer connection portion and the scan head connection portion being a single element.

In another embodiment, an ultrasound probe is provided that includes a housing and a scan head within the housing, wherein the scan head includes a transducer array. The ultrasound probe further includes an axle coupled to the scan head allowing rotation of the scan head and at least one processing or control board. The ultrasound probe also includes a connection member interconnecting the transducer array and the processing or control board, wherein the connection member is a single element.

In a further embodiment, a method for providing a connection member for an ultrasound probe is provided. The method includes forming a transducer flex portion and a scan head flex portion as a single connection member and bending the connection member to extend around components within a scan head of an ultrasound probe and extend from the scan head.

BRIEF DESCRIPTION OF THE DRAWINGS

FIG. 3 is a partial cross-sectional view of a portion of the ultrasound probe in FIG. 1 showing a connection arrangement.

FIG. 4 is a diagram illustrating a connection member formed in accordance with various embodiments.

FIG. 5 is a diagram of the connection member of FIG. 4 in an assembled condition.

DETAILED DESCRIPTION

Figure 1:
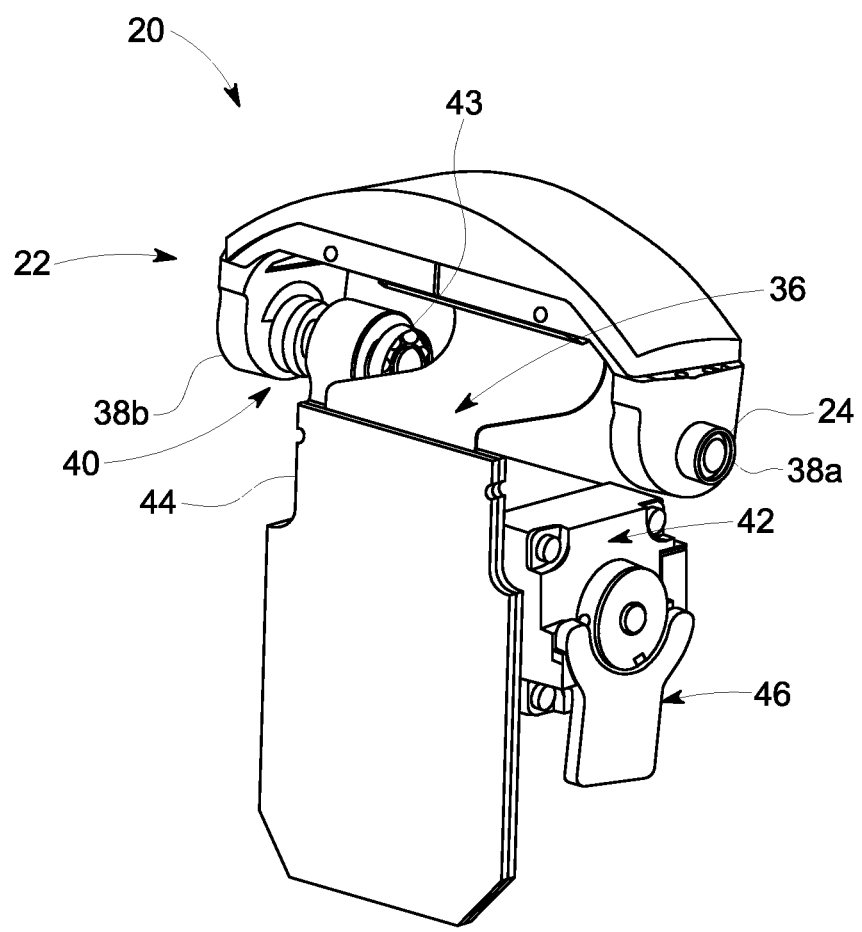
FIG. 1 is a perspective view of a portion of an ultrasound probe in accordance with an embodiment having the probe housing removed.

The following detailed description of various embodiments will be better understood when read in conjunction with the appended drawings. To the extent that the figures illustrate diagrams of structural or functional blocks of the various embodiments, the blocks are not necessarily indicative of the division between hardware or circuitry. Thus, for example, one or more of the blocks may be implemented in a single piece of hardware or multiple pieces of hardware. It should be understood that the various embodiments are not limited to the arrangements and instrumentality shown in the drawings.

Described herein are various embodiments provide an interconnection arrangement for an ultrasound probe wherein a single part or piece is provided for both transducer connection and scan head connection. For example, in one embodiment, a transducer flexible printed circuit board (also referred to herein as flex PCB or flex) and a scan head flex are provided in a single part or single element such that a single integrated connection arrangement is provided. By practicing at least one embodiment, a smaller probe or miniaturization of the probe may be provided.

It should be noted that although the various embodiments are described in connection with a probe having a particular mechanical configuration, the connection arrangement of the various embodiments may be provided in different types and configurations of probes.

Figure 2:
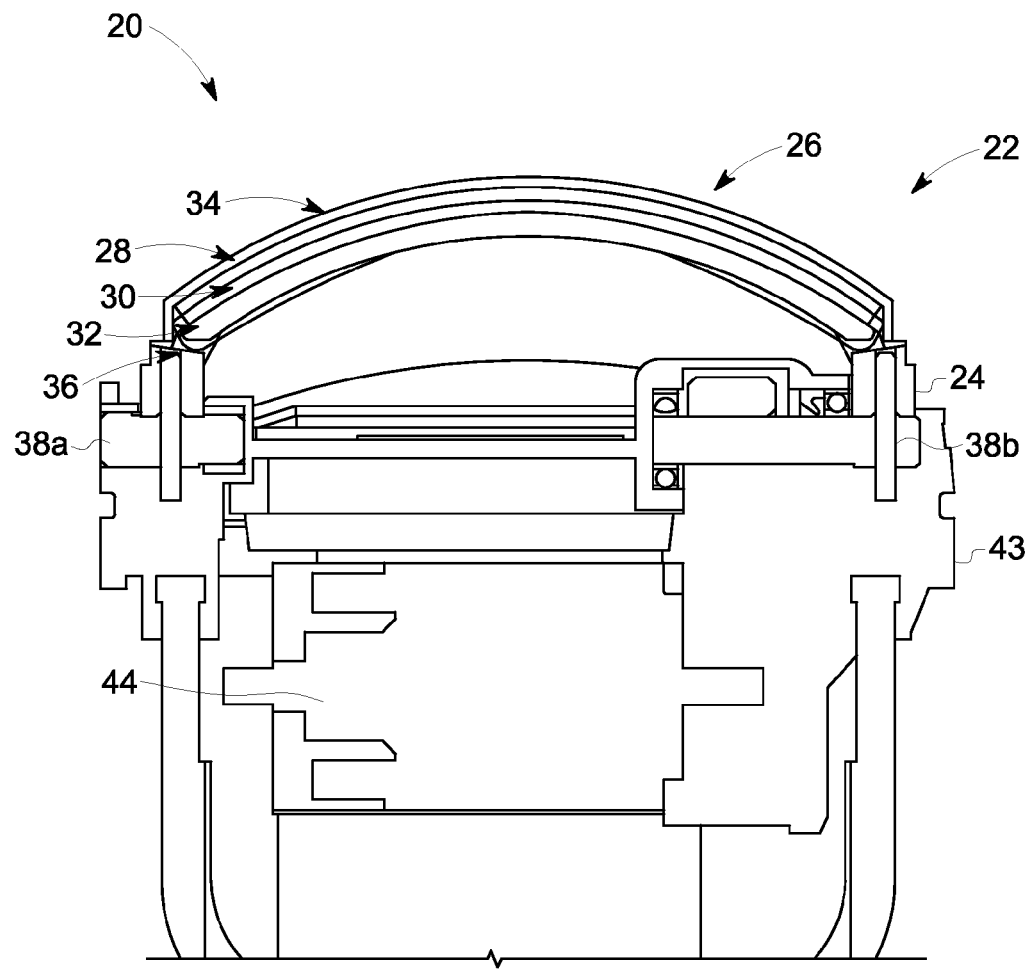
FIG. 2 is a cross-sectional view of a portion of the ultrasound probe in FIG. 1.

In particular, various embodiments provide an ultrasound probe 20, a portion of which, namely a scanning end 22, is shown in FIGS. 1-3. The ultrasound probe 20 in the illustrated embodiment is a volume imaging probe having a mechanically moving scan head 24 (which defines a transducer carrier or bridge for supporting a transducer array 26) within a scan head housing, such as a chamber 104 (shown in FIGS. 8-10). The transducer array 26 may be formed from any suitable components, for example, a piezoelectric ceramic 28 and a backing strip 30 (or backing layer) as shown more clearly in FIG. 2, which is supported on a carrier member 32.

The scan head housing in one embodiment defines a wet chamber of the ultrasound probe 20 with a separate dry chamber having contained therein drive means for mechanically controlling (e.g., rotating) the scan head 24 to move the transducer array 26, which may be covered by a lens 34. Means for communicating with and electrically controlling the transducer array 26 are also provided as described in more detail herein, which generally includes a single connection member 36 defining a connector, which in one embodiment is a single element (e.g., a unitary construction) having a combined or integrated transducer and scan head flex PCB. Accordingly, the connection to the scan head 24 and the connection within the scan head 24 to the transducer array 26 are provided using a single element, such as a single flex PCB that is configured to be deformed, in particular folded, as described herein to provide the interconnection.

It should be noted that although the transducer array 26 is shown as a curved array element, different configurations may be provided. For example, the transducer array 26 may be a linear array.

In one embodiment, the scan head 24 may be in a chamber having an acoustic liquid therein and includes transducer driving means for moving (e.g., rotating) the transducer array 26 and transducer control means for selectively driving elements of the transducer array 26 (e.g., the piezoelectric ceramic 28 of the transducer array 26). The transducer driving means generally includes a transducer axle 38 in connection with the scan head 24, for example, coupled to the scan head 24 and extending within a drive shaft opening formed within the scan head 24. It should be noted that the carrier member 32 in various embodiments also defines a connector support member within the scan head 24 for supporting the flex PCB (forming the connection member 36) in connection with the transducer array 26.

The scan head 24 generally defines a transducer carrier or transducer bridge, such that when the transducer axle 38 moves, in particular rotates, to move the scan head 24, movement of the transducer array 26 mounted thereto is also provided. It should be noted that the connection member 36 is coupled to the transducer array 26 (e.g., laminated with the transducer array 26), such that the connection member 36 is electrically connected to the transducer array 26.

It also should be noted that different configurations may be provided. For example, although the scan head 24 as shown in FIG. 1 may be mounted to two separate transducer axles 38a and 38b that do not extend entirely between the side walls of the scan head 24, different sizes of transducer axles may be provided. Additionally, in some embodiments, a single transducer axle 38 may be provided. In the illustrated embodiment, the transducer axle 38b extends about a third of the total distance between the side walls and engages a gear arrangement 40, which in this embodiment is a toothed gear arrangement coupled to a motor 42.

However, other arrangements to drive the transducer axle 38b may be provide, for example, a ball drive arrangement or a two-stage gear arrangement having a belt drive and a rope drive. Additionally, a ball bearing 43 is provided in connection with the transducer axle 38b, which reduces rotational friction and supports radial and axial loads. In this embodiment, a ball bearing 43 is also provided in connection with the transducer axle 38a on an opposite side of the scan head 24. The transducer axle 38a extends within the side wall of the scan head 24 and outward therefrom a distance sufficient to support the ball bearing 42. Accordingly, the transducer axle 38a is shorter than the transducer axle 38b in the illustrated embodiment. However, the lengths and dimensions of the transducer axles 38 are merely for illustration, and transducer axles 38 having different lengths, dimensions or configurations may be provided.

The transducer array 26 is in connection with one or more processing or control boards 44 via the connection member 36 that provide communication therebetween. For example, the one or more processing or control boards 44 may be tuning and/or termination boards for the transducer array 26, which may be formed from rigid PCBs. However, any other type of processing or control board may be provided as desired or needed. Other components also may be provided in some embodiments. For example, in one embodiment, an alignment sensor 46 may be provided, which may be a Hall sensor PCB that operates to provide center position alignment of the transducer array 26.

In one embodiment, the connection member 36 may be provided as shown in FIGS. 4 and 5, in an uninstalled or unassembled configuration and an installed or assembled configuration, respectively. In the installed or assembled configuration shown in FIG. 5, the connection member 36 is deformed, in particular, folded or bent (or rolled) or arranged to allow connection between the transducer array 26 and the processing or control boards 44.

In the illustrated embodiment, the connection member 36 is a single element, such as a single piece of flex PCB that includes a transducer connection portion 50 and scan head connection portions 52. In general, and as described in more detail below, this single integrated configuration provides for connection to the transducer array 26 with the transducer connection portion 50, and connection from the scan head 24 to other portions within the probe (e.g., the processing or control boards 44) with the scan head connection portions 52, respectively.

In the illustrated embodiment, the transducer connection portion 52 has a length (L) and width (W) that is complementary to the transducer array 26. For example, in various embodiments, the transducer connection portion 50 is sized and shaped to allow for connection with the transducer array 26. In one embodiment, the dimensions and shape of the transducer connection portion 50 are provided such that the transducer connection portion 50 may be coupled within, in particular, laminated within, the acoustic stack forming the transducer array 26.

Similarly, the scan head connection portions 52 are sized and shaped for connection to other components within the probe 20, for example, the processing or control boards 44, such as the rigid PCBs that form the processing or control boards 44. In the illustrated embodiment, the transducer connection portion 50 is generally longer and narrower than each of the scan head connection portions 52. However, the lengths and widths of the transducer connection portion 50 and the scan head connection portions 52 may be varied as desired or needed.

In the illustrated embodiment, the scan head connection portions 52 generally form ends of the connection member 36. For example, the scan head connection portions 52 may be formed at ends of extensions or arms 54 that extend from the transducer connection portion 50. It should be noted that the different portions of the connection member 36 are generally aligned along a single axis such that connection member 36 is a single linear piece of PCB. Thus, in one embodiment, the connection member 36 generally includes a middle tab defining the transducer connection portion 50 and end tabs defining the scan head connection portions 52.

It also should be noted that the connection member 36 may be formed from one or more layers of material. In various embodiments, the connection member 36 or portions thereof are formed from one or more layers of copper. However, different materials may be used. In particular, the transducer connection portion 50 in various embodiments is formed from any suitable acoustically transparent material. For example, in one embodiment, the transducer connection portion 50 is formed from copper, which may be a dual layer or two layer copper arrangement, with one layer defining a signal plane and one layer defining a ground plane. The extensions or arms 54 and the scan head connection portions 52 in one embodiment are formed from a single metal layer, for example, a single copper layer, which also forms the transducer connection portion 50. In the illustrated embodiment, the signal plane is single layer that extends from one end of the connection member 36 to the other end of the connection member 36, for example, from one scan head connection portion 52 to the other scan head connection portion 52.

Figure 6:
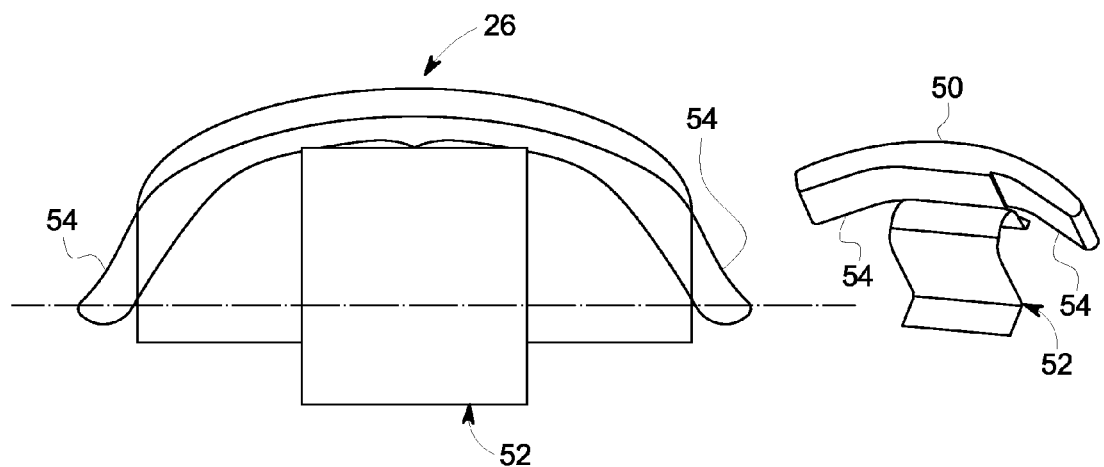
FIG. 6 is a diagram illustrating bending of the connection member of FIG. 4.

The connection member 36 is shown assembled in an installed condition or state in FIG. 5. In particular, the transducer connection portion 50 is bent to conform to the shape of the transducer array 26, for example, for laminating within the acoustic stack of the transducer array 26. The scan head connection portions 52 are folded and bent around the mechanical parts in the scan head 24 as shown more clearly in FIG. 6. As can be seen, the extensions or arms 54 are folded around mechanical parts as shown in FIG. 3 and the scan head connection portions 52 defining the ends of the connection member 36 are folded on top of each other and extend in the azimuth direction (illustrated by the arrows 56) to the connect, for example, to the processing or control boards 44. The ends, namely the scan head connection portions 52 allow connection of the scan head 24 to other components within the probe 24 and may, for example, be clamped on top of each other. In one embodiment, the ends of the connection member 36 may be bent to form generally planar surfaces 58 for interconnection to the processing or control boards 44.

Thus, the connection member 36 is a single transducer and scan head flex allowing connection to the transducer array 26 and extending from the scan head 24, such as for connection to the processing or control boards 44. As described above, the transducer flex and scan head flex are integrated or combined into a single part. Thus, one connection piece may be used to interconnect the transducer array 26 with other components within the probe 20.

In the illustrated embodiment, for a curved transducer array 26, the flex portions forming the connection member 36 are routed to the azimuthal end of the transducer array 26 and folded back to allow for exit from the transducer, in particular, the scan head 24. Thus, in various embodiments, the connection member 36 provides a configuration allowing for connection using a azimuthal exit from the scan head 24 instead of an elevational exit.

In various embodiments, the azimuthal end exit configuration of the connection member 36 has a reduced cross-section and thus reduces liquid friction during 4D modes of operation of the probe 20, which can provide reduced motor load and a smaller design.

The various layers and structure of the connection member 36 may be modified as desired or needed. However, in one embodiment, the connection member 36 includes a single metal layer only in the scan head flex region (defining the scan head connection portions 52 and arms 54) to provide mechanical characteristics for the dynamic bending. Moreover, in one embodiment, the connection member 36 includes two or more metal layers outside of the scan head flex section (defining the transducer connection portion 50) to allow for ground interconnection and, for example, EMI/EMC shielding.

Figure 7:
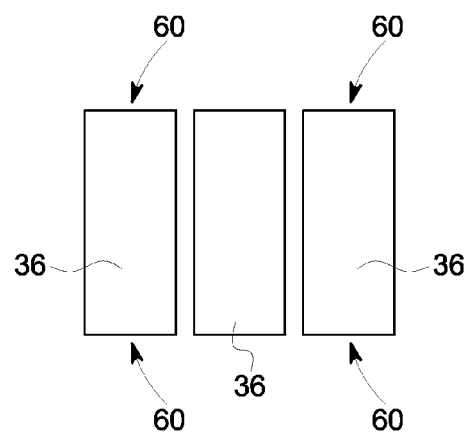
FIG. 7 is a diagram illustrating a configuration for manufacturing multiple connection members in accordance with various embodiments.

It should be noted that the connection member 36 may be formed in a single manufacturing step or multiple manufacturing steps. During manufacturing, multiple connection members 36 may be formed next to each other (e.g., adjacent to each other) as shown in FIG. 7 (illustrated generally as rectangular elements for simplicity and ease of illustration), with routing of traces provided at the ends 60 of the connection members 36. Accordingly, in some embodiments, smaller and/or finer pitch traces may be used.

Figure 8:
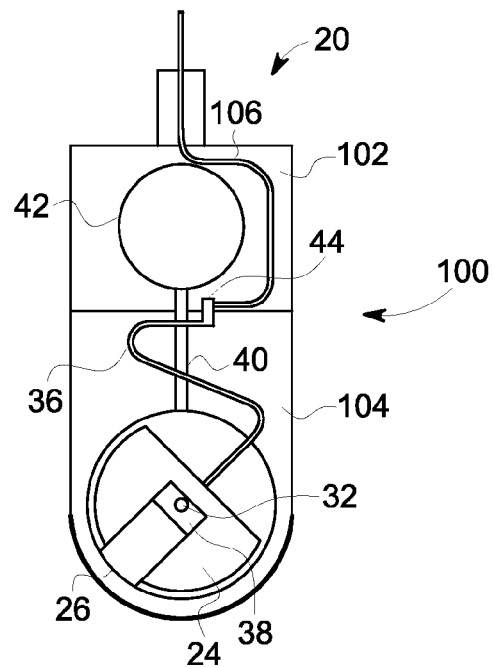
FIGS. 8-10 are diagrams of an ultrasound probe in accordance with one embodiment showing a moving scan head.
Figure 9:
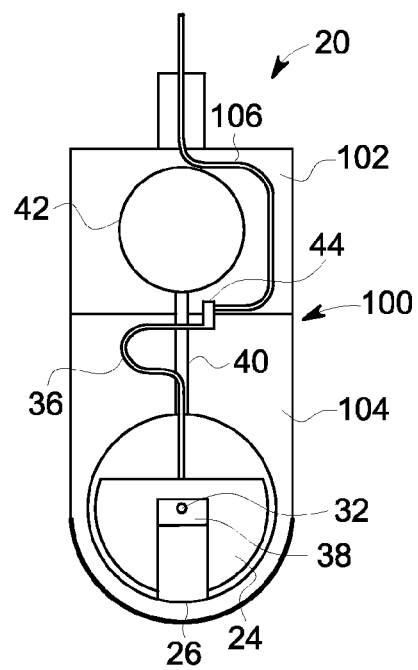
Figure 10:
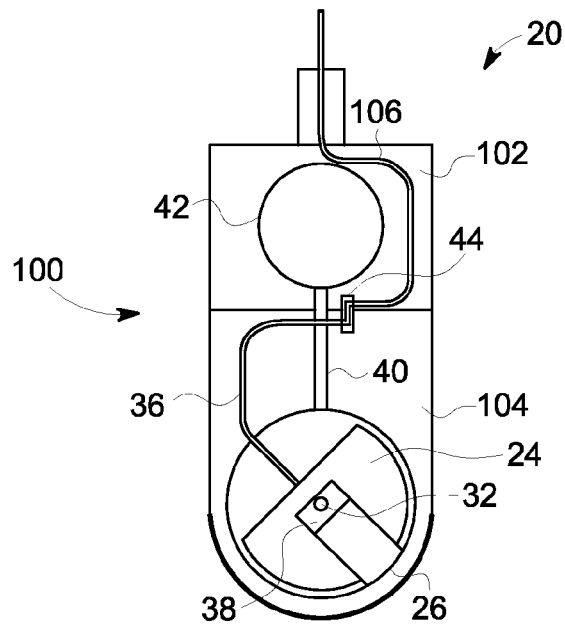

FIGS. 8-10 illustrate one embodiment of the ultrasound probe 20 showing operation of the elements of a moving transducer array 26. In particular, these Figures illustrate the transducer array 26 in different rotational positions. The ultrasound probe 20 is a volume imagining probe that may be in communication with a host system.

In one embodiment, the probe 20 includes a housing 100 having a first chamber 102 (e.g., a dry chamber) and a second chamber 104 (e.g., a wet chamber). The first chamber 102 and second chamber 104 may be formed as a single unit (e.g., unitary construction) or may be formed as separate units connected together (e.g. modular design). In an exemplary embodiment, the first chamber 102 is a dry or air chamber having contained therein drive means for mechanically controlling the transducer array 26 and communication means for electrically controlling the transducer array 26. The drive means generally includes the motor 42 (e.g., stepper motor) and the gear arrangement 40 (shown in FIG. 2). The communication means generally includes a system cable 106 connected to the processing or control boards 44 to communicate with the host system to drive the elements of the transducer array 26 (e.g., selectively activate the elements of the transducer array 26).

However, it should be noted that in some embodiments, only a single dry chamber is provided. It also should be noted that although the drive means and communication means are described herein having specific component parts, they are not so limited. For example, the drive means may have a different gear arrangement and the communication means may have different connection members or transmission lines.

In the illustrated embodiment, the second chamber 104 is a wet chamber (e.g., chamber having acoustic liquid therein) having contained therein transducer driving means for moving (e.g., rotating) the transducer array 26 and transducer control means for selectively driving elements of the transducer array 26 (e.g., the piezoelectric ceramics). The transducer driving means generally includes drive means as described herein.

The transducer control means generally includes the connection member 36 for interconnecting the transducer array 26 in the scan head 24 with the processing or control boards 44. As described herein, the connection member 36 is a single structure, such as a single flex PCB structure that combines the transducer flex PCB and the scan head flex PCB. The connection member 36 generally includes one or more communication lines for providing communication therebetween. In one exemplary embodiment, the connection member 36 interconnects the system cable 106 and the flex PCBs via the processing or control boards 44 through a sealing member 110 (shown in FIG. 3 as a bushing unit) that provides a liquid tight seal between the first chamber 102 and the second chamber 104. The sealing member 110 may be, for example, a bushing unit.

It should be noted that although the transducer driving means and transducer control means are described herein having specific component parts, these elements are not so limited. For example, the transducer driving means may have a different shaft arrangement and the transducer control means may have different control circuits or transmission lines. It also should be noted that additional or different component parts may be provided in connection with the probe 20 as needed or desired, and/or based upon the particular type and application of the probe 20. It further should be noted that the transducer array 26 may be configured for operation in different modes, such as, for example, a 1D, 1.25D, 1.5D, 1.75D, 2D, 3D and 4D modes of operation.

Figure 11:
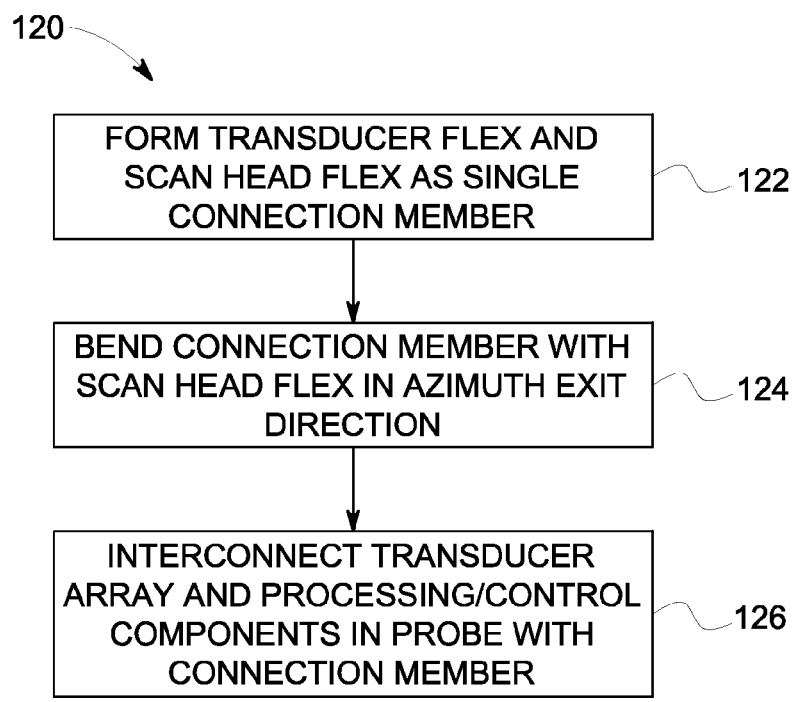
FIG. 11 is a flowchart of a method for providing a connection arrangement for a transducer array in an ultrasound probe in accordance with various embodiments.

Various embodiments also provide a method 120 as shown in FIG. 11 for providing a connection arrangement for a transducer array in an ultrasound probe. The method 120 includes forming a transducer flex and a scan head flex as a single connection member at 122. For example, a single metal layer may be used to form the scan head flex with one or more additional metal layers forming the transducer flex. In one embodiment, the single metal layer is a planar piece of copper with communication traces etched therein. The single metal layer forms the signal plane that provides communication with the transducer array from outside the scan head. The additional metal layer(s) of the transducer flex defines a ground plane. It should be noted that in some embodiments more than one metal layer may be used to form the signal plane. However, each of the metal layers are single pieces of planar metal coupled together, such as in a stacked arrangement.

The method 120 further includes bending the connection member at 122 such that when installed within an ultrasound provides the scan head flex extends in an azimuth exit direction in some embodiments. In particular, the transducer flex is bent or curved to conform to the shape of a transducer array, for example, a curved transducer array. The scan head flex are also shaped to extend around the mechanical components of the scan head and then to exit in the azimuth direction as described in more detail herein. It should be noted that the transducer flex may be laminated as part of the transducer array.

The formed connection member is then installed within an ultrasound probe. For example, at 124 the connection member may be installed within an ultrasound probe to interconnect the transducer array with processing components or control components in the probe. The coupling with the processing components or control components may be provided using any suitable connection means, such as using solder.

Figure 12:
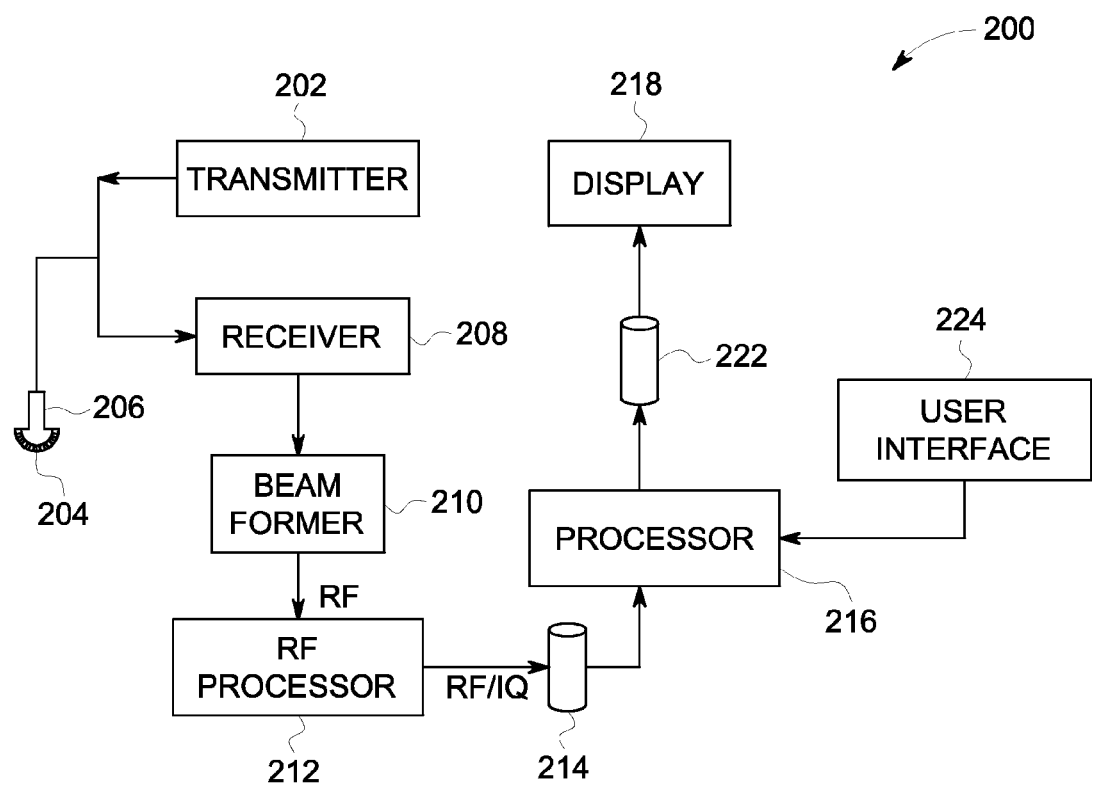
FIG. 12 is a block diagram of an ultrasound system in accordance with one embodiment.

The various embodiments described herein may be implemented in connection with an imaging system shown in FIG. 12. Specifically, FIG. 12 illustrates a block diagram of an exemplary ultrasound system 200 that is formed in accordance with various embodiments. The ultrasound system 200 includes a transmitter 202, which drives a plurality of transducers 204 within an ultrasound probe 206 to emit pulsed ultrasonic signals into a body. A variety of geometries may be used. For example, the probe 206 may be used to acquire 2D, 3D, or 4D ultrasonic data, and may have further capabilities such as 3D beam steering. Other types of probes 206 may be used. The probe 206 also may be embodied as the probe 20 described herein having the connection member 36. The ultrasonic signals are back-scattered from structures in the body, like blood cells or muscular tissue, to produce echoes which return to the transducers 204. The echoes are received by a receiver 208. The received echoes are passed through a beamformer 210, which performs beamforming and outputs an RF signal. The beamformer may also process 2D, 3D and 4D ultrasonic data. The RF signal then passes through an RF processor 212. Alternatively, the RF processor 212 may include a complex demodulator (not shown) that demodulates the RF signal to form IQ data pairs representative of the echo signals. The RF or IQ signal data may then be routed directly to RF/IQ buffer 214 for temporary storage.

The ultrasound system 200 also includes a signal processor 216. The signal processor 216 processes the acquired ultrasound information (i.e., RF signal data or IQ data pairs) and prepares frames of ultrasound information for display on a display 218. The signal processor 216 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 214 during a scanning session and processed in less than real-time in a live or off-line operation. A user interface, such as user interface 224, allows an operator to enter data, enter and change scanning parameters, access protocols, select image slices, and the like. The user interface 224 may be a rotating knob, switch, keyboard keys, mouse, touch screen, light pen, or any other suitable interface device.

The ultrasound system 200 may continuously acquire ultrasound information at a frame rate that exceeds 50 frames per second—the approximate perception rate of the human eye. The acquired ultrasound information, which may be the 3D volume dataset, is displayed on the display 218. The ultrasound information may be displayed as B-mode images, M-mode, volumes of data (3D), volumes of data over time (4D), or other desired representation. An image buffer (e.g., memory) 222 is included for storing processed frames of acquired ultrasound information that are not scheduled to be displayed immediately. The image buffer 222 in one embodiment is of sufficient capacity to store at least several seconds worth of frames of ultrasound information. The frames of ultrasound information are stored in a manner to facilitate retrieval thereof according to its order or time of acquisition. The image buffer 222 may comprise any known data storage medium.

Figure 13:
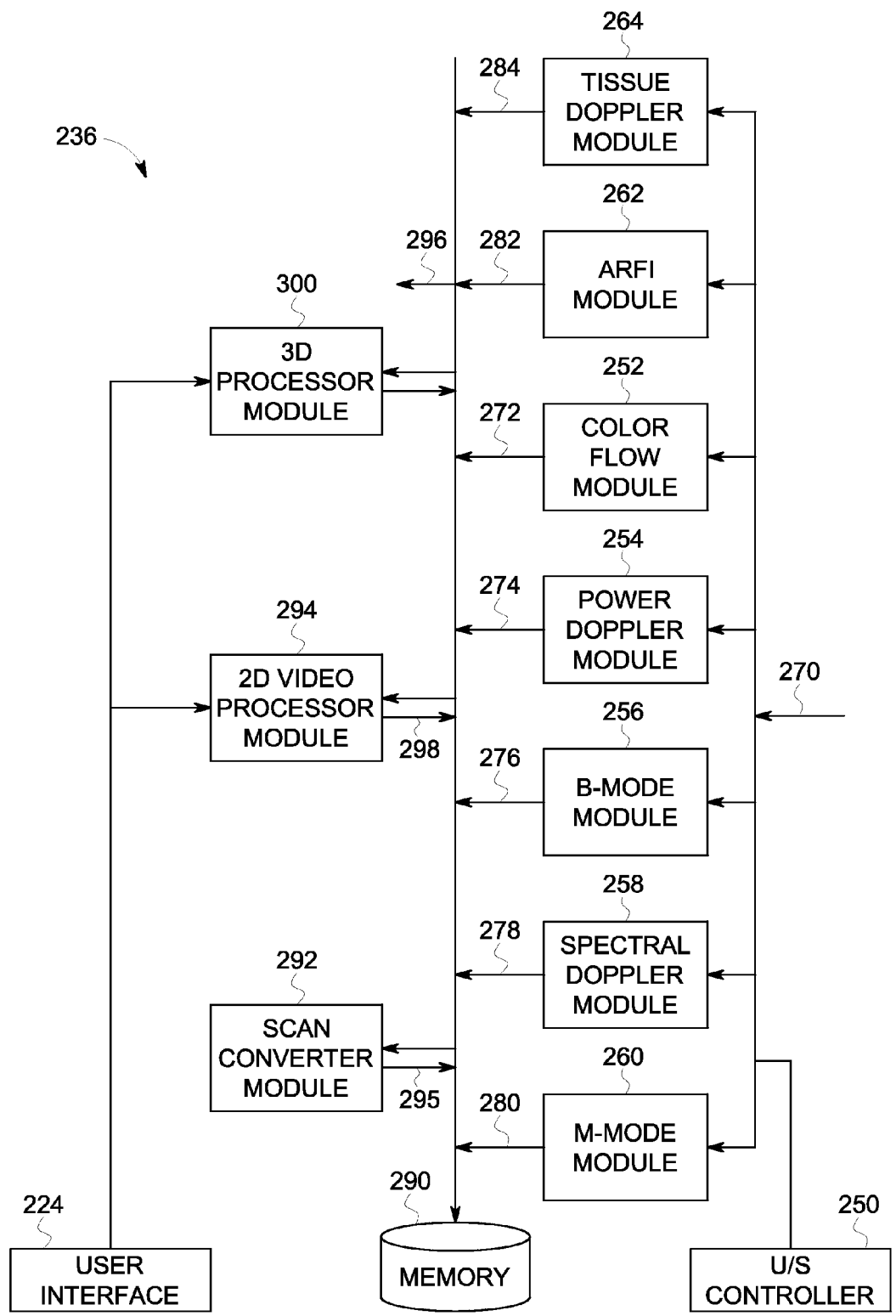
FIG. 13 is a block diagram of an ultrasound processor module of the ultrasound system of FIG. 12 formed in accordance with various embodiments.

FIG. 13 illustrates an exemplary block diagram of an ultrasound processor module 236, which may be embodied as the signal processor 216 of FIG. 12 or a portion thereof. The ultrasound processor module 236 is illustrated conceptually as a collection of sub-modules, but may be implemented utilizing any combination of dedicated hardware boards, DSPs, processors, etc. Alternatively, the sub-modules of FIG. 8 may be implemented utilizing an off-the-shelf PC with a single processor or multiple processors, with the functional operations distributed between the processors. As a further option, the sub-modules of FIG. 13 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 13 may be controlled by a local ultrasound controller 250 or by the processor module 236. The sub-modules 252-264 perform, for example, mid-processor operations. The ultrasound processor module 236 may receive ultrasound data 270 in one of several forms. In the embodiment of FIG. 13, the received ultrasound data 270 constitutes I,Q data pairs representing the real and imaginary components associated with each data sample. The I,Q data pairs are provided to one or more of a color-flow sub-module 252, a power Doppler sub-module 254, a B-mode sub-module 256, a spectral Doppler sub-module 258 and an M-mode sub-module 260. Optionally, other sub-modules may be included such as an Acoustic Radiation Force Impulse (ARFI) sub-module 262 and a Tissue Doppler (TDE) sub-module 264, among others.

Each of sub-modules 252-264 are configured to process the I,Q data pairs in a corresponding manner to generate color-flow data 272, power Doppler data 274, B-mode data 276, spectral Doppler data 278, M-mode data 280, ARFI data 282, and tissue Doppler data 284, all of which may be stored in a memory 290 (or memory 214 or memory 222 shown in FIG. 12) temporarily before subsequent processing. For example, the B-mode sub-module 256 may generate B-mode data 276 including a plurality of B-mode image planes, such as in a biplane or triplane image acquisition as described in more detail herein.

The data 272-284 may be stored, for example, as sets of vector data values, where each set defines an individual ultrasound image frame. The vector data values are generally organized based on the polar coordinate system.

A scan converter sub-module 292 accesses and obtains from the memory 290 the vector data values associated with an image frame and converts the set of vector data values to Cartesian coordinates to generate an ultrasound image frame 295 formatted for display. The ultrasound image frames 295 generated by the scan converter module 292 may be provided back to the memory 290 for subsequent processing or may be provided to the memory 214 or the memory 222 (both shown in FIG. 12).

Once the scan converter sub-module 292 generates the ultrasound image frames 295 associated with, for example, B-mode image data, and the like, the image frames may be restored in the memory 290 or communicated over a bus 296 to a database (not shown), the memory 214, the memory 214 and/or to other processors.

The scan converted data may be converted into an X,Y format for video display to produce ultrasound image frames. The scan converted ultrasound image frames are provided to a display controller (not shown) that may include a video processor that maps the video to a gray-scale mapping for video display. The gray-scale map may represent a transfer function of the raw image data to displayed gray levels. Once the video data is mapped to the gray-scale values, the display controller controls the display 218 (shown in FIG. 12), which may include one or more monitors or windows of the display, to display the image frame. The image displayed in the display 218 is produced from image frames of data in which each datum indicates the intensity or brightness of a respective pixel in the display.

Referring again to FIG. 13, a 2D video processor sub-module 294 combines one or more of the frames generated from the different types of ultrasound information. For example, the 2D video processor sub-module 294 may combine a different image frames by mapping one type of data to a gray map and mapping the other type of data to a color map for video display. In the final displayed image, color pixel data may be superimposed on the gray scale pixel data to form a single multi-mode image frame 298 (e.g., functional image) that is again re-stored in the memory 290 or communicated over the bus 296. Successive frames of images may be stored as a cine loop in the memory 290 or memory 214 (shown in FIG. 12). The cine loop represents a first in, first out circular image buffer to capture image data that is displayed to the user. The user may freeze the cine loop by entering a freeze command at the user interface 224. The user interface 224 may include, for example, a keyboard and mouse and all other input controls associated with inputting information into the ultrasound system 200 (shown in FIG. 12).

A 3D processor sub-module 300 is also controlled by the user interface 224 and accesses the memory 290 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

The ultrasound system 200 of FIG. 12 may be embodied in a small-sized system, such as laptop computer or pocket sized system as well as in a larger console-type system.

Thus, various embodiments provide an ultrasound probe having a connection member that combines a transducer flex and scan head flex into a single piece design.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive, optical disk drive, and the like. The storage device may also be other similar means for loading computer programs or other instructions into the computer or processor.

As used herein, the term "computer" or "module" may include any processor-based or microprocessor-based system including systems using microcontrollers, Reduced Instruction Set Computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A connector for an ultrasound probe, the connector comprising:
   a transducer connection portion configured to couple to a transducer of an ultrasound probe; and
   a scan head connection portion configured to extend from a scan head of the ultrasound probe containing the transducer, the transducer connection portion and the scan head connection portion being a single element with end tabs defining the scan head connection portion and a middle tab between the end tabs defining the transducer connection portion, the end tabs folded on top of each other, wherein the transducer connection portion and the scan head connection portion comprise a flexible circuit board.

2. The connector of claim 1, wherein arms extend between the transducer connection portion and the scan head connection portion.

3. The connector of claim 1, wherein the transducer connection portion is at least one of sized or shaped for laminating within an acoustic stack of a transducer array.

4. The connector of claim 1, wherein the end tabs and the middle tab extend along a single axis.

5. The connector of claim 1, wherein the scan head connection portion is bendable with respect to the transducer connection portion, wherein the scan head extends along a scan head direction and the scan head connection portion extends from the scan head transversely to the scan head direction.

6. An ultrasound probe comprising:
   a housing;
   a scan head within the housing, the scan head including a transducer array;
   an axle coupled to the scan head allowing rotation of the scan head;
   at least one processing or control board; and
   a connection member interconnecting the transducer array and the processing or control board, the connection member being a single element configured for connection to the at least one processing or control board, wherein the connection member comprises two end tabs defining a scan head connection portion configured to extend from the scan head and a middle tab between the end tabs defining a transducer connection portion configured to couple to the transducer array of the scan head, wherein the end tabs are folded on top of each other.

7. The ultrasound probe of claim 6, wherein the connection member comprises a single planar metal layer.

8. The ultrasound probe of claim 6, wherein the scan head connection portion is coupled to the processing or control board, with arms extending between the transducer connection portion and scan head connection portion.

9. The ultrasound probe of claim 6, wherein the transducer connection portion is at least one of sized or shaped for laminating within an acoustic stack of the transducer array.

10. The ultrasound probe of claim 6, wherein the end tabs and the middle tab extend along a single axis.

11. The ultrasound probe of claim 6, wherein the connection portion is bent around one or more components within the scan head and bent to route the connection portion to exit from the scan head transversely to the scan head direction.

12. The ultrasound probe of claim 6, wherein the single element comprises a single metal layer and further comprising at least one additional metal layer in the transducer connection portion, wherein the single metal layer is a signal plane and the additional metal layer is a ground plane.

13. The ultrasound probe of claim 6, wherein the transducer array is operable in one of a three-dimensional (3D) or a four-dimensional (4D) imaging mode.

14. The ultrasound probe of claim 6, wherein the housing comprises a wet chamber and a dry chamber, the transducer array being in the wet chamber.

15. A method for providing a connection member for an ultrasound probe having a scan head with a transducer array, the method comprising:
   forming a single connection member comprising a transducer flex portion and a scan head flex portion, the transducer flex portion formed by a middle tab of the connection member, and the scan head flex portion formed from two end tabs of the connection member;
   bending the connection member so that the transducer flex portion extends around components within a scan head along a scan head direction of the ultrasound probe; and
   folding the end tabs of the connection member forming the scan head flex portion on to of each other and bending the connection member such that the scan head flex portion extends away from the transducer array transversely to the scan head direction.

16. The method of claim 15, wherein the transducer flex portion and the scan head flex portion comprise a flexible circuit board.

17. A connector for an ultrasound probe, the connector comprising:
   a transducer connection portion configured to couple to a transducer of an ultrasound probe; and
   a scan head connection portion configured to extend from a scan head of the ultrasound probe containing the transducer, wherein the transducer connection portion and the scan head connection portion being a single element with end tabs defining the scan head connection portion and a middle tab between the end tabs defining the transducer connection portion, the end tabs folded on top of each other, wherein the single element comprises a single metal layer and further comprising at least one additional metal layer in the transducer connection portion, wherein the single metal layer is a signal plane and the additional metal layer is a ground plane.

* * * * *